(12) United States Patent
Vijay et al.

(10) Patent No.: US 8,524,770 B2
(45) Date of Patent: Sep. 3, 2013

(54) WOOL CARE COMPOSITION

(75) Inventors: Veer Vijay, Gwalior (IN); Prakash Shri, Gwalior (IN); Chandel Kshitij, Gwalior (IN); Jaywantrao Mendki Murlidhar, Gwalior (IN); Vijayaraghavan Rajagopalan, Gwalior (IN); Krishnamurthy Sekhar, New Delhi (IN)

(73) Assignee: Director General, Defence Research & Development Organization, Ministry of Defence, Government of India (IN)

( * ) Notice: Subject to any disclaimer, the term of this patent is extended or adjusted under 35 U.S.C. 154(b) by 186 days.

(21) Appl. No.: 13/146,554

(22) PCT Filed: Nov. 20, 2009

(86) PCT No.: PCT/IN2009/000670
§ 371 (c)(1),
(2), (4) Date: Jul. 27, 2011

(87) PCT Pub. No.: WO2010/086872
PCT Pub. Date: Aug. 5, 2010

(65) Prior Publication Data
US 2011/0305644 A1 Dec. 15, 2011

(30) Foreign Application Priority Data
Jan. 29, 2009 (IN) .............................. 167/DEL/2009

(51) Int. Cl.
| A01N 25/00 | (2006.01) |
| A01N 25/24 | (2006.01) |
| A01N 65/00 | (2009.01) |
| A01N 53/00 | (2006.01) |
| D06M 16/00 | (2006.01) |
| D06M 13/02 | (2006.01) |
| D06M 23/06 | (2006.01) |
| D06M 13/00 | (2006.01) |
| D06M 15/263 | (2006.01) |
| A01N 37/38 | (2006.01) |
| A01N 53/08 | (2006.01) |
| A61K 9/12 | (2006.01) |

(52) U.S. Cl.
USPC .............. 514/521; 424/45; 424/407; 514/65; 514/68; 514/531; 442/125

(58) Field of Classification Search
USPC .............. 514/521, 65, 68, 531; 424/45, 407; 442/125
See application file for complete search history.

(56) References Cited

U.S. PATENT DOCUMENTS
| 5,178,782 A | 1/1993 | Yodice et al. |
| 2005/0132500 A1 | 6/2005 | Ulrich et al. |
| 2008/0090780 A1 | 4/2008 | Sanson et al. |

FOREIGN PATENT DOCUMENTS
| CN | 101372809 A * | 2/2009 |
| EP | 0382382 | 8/1990 |
| WO | 9700610 | 1/1997 |
| WO | 9723682 | 7/1997 |
| WO | 2006117702 | 2/2006 |
| WO | 2006107905 | 4/2006 |
| WO | 2006059152 | 6/2006 |

OTHER PUBLICATIONS

International Preliminary Report on Patentability in PCT/IN2009/000670, dated May 3, 2011.
International Search Report in PCT/IN2009/000670, dated Mar. 30, 2010.

* cited by examiner

*Primary Examiner* — John Pak
*Assistant Examiner* — Nathan W Schlientz
(74) *Attorney, Agent, or Firm* — McAndrews, Held & Malloy, Ltd.

(57) ABSTRACT

The present invention relates to a wool care composition comprising pyrethroid insecticide, a copolymer and a solvent wherein the said copolymer binds with the solvent and pyrethroid insecticide. This composition can be an improved aerosol spray formulation for treating of pure or blended woollen clothing and textile, fur and feather lined garments and other keratinous items for protection or insect proofing from various types of insect pests both clothes moths and carpet beetles during their storage, transport and use. Wool care aerosol solution can be sprayed with pressurized container having either a propellant as ready-to-use aerosol or manually operated sprayers. The aerosol spray composition may also contain fragrance and solvent. The other components in the composition are at least one copolymer/emulsifier and/or dispersant.

18 Claims, No Drawings

WOOL CARE COMPOSITION

The present application is filed pursuant to 35 U.S.C. 371 as a U.S. National Phase application of International Patent Application No. PCT/IN2009/000670, which was filed Nov. 20, 2009, claiming the benefit of priority to Indian Patent Application No. 167/DEL/2009, which was filed on Jan. 29, 2009. The entire text of the aforementioned applications is incorporated herein by reference in its entirety.

TECHNICAL FIELD

This invention relates to a wool care composition comprising pyrethroid insecticide, a copolymer and a solvent wherein the said copolymer binds with the solvent and pyrethroid insecticide. The wool care composition can be an aerosol spray composition for protection (insect proofing) of pure or blended woollen items, fur and feathers lined garments, and other keratinous items from various species of insect pests, more specifically but without implying any limitation thereto, to protect such items, during their storage, use and transport from various types of insect species of woollen pests.

BACKGROUND

Woollen articles made of pure (100%) wool fibres or blended with natural or synthetic fibres like polyester, viscose rayon, cotton, etc. or both in different proportion such as apparel, carpet, durries, felt etc. and fur-feather lined garments are highly susceptible to insect damage, and are frequently damaged or destroyed by various insect species of wool pests in commercial, industrial and domestic stores and also during their use and transport. Sometimes this damage result into colossal loss to the stored woollen items. Unprotected keratinous items such as sikhar trophies, animal skins, upholstered furniture and stuffed animal museum specimens are also damaged by these wool pests.

The wool pests are of two types, carpet beetles and clothes moths which commonly found damaging woollen and fur and feathers items. The carpet beetle species are *Anthrenus flavipes, Anthrenus verbasci, Anthrenus coloratus, Anthrenus oceanicus, Attagenus fasciatus, Attagemis cyphonoides, Attagemis lobatus, Attagemis indicus* and *Attagenus birmanicus*. The clothes moths species are *Tinea transhtcens, Tinea pellionella, Tinea dubiella* and *Tineola bisselliella*. These pests cause maximum damage during their larval stage to the woollen, fur-feather lined items and other keratinous items in stores or when these items are left unattended for longer period and also during their use and transport.

Conventionally naphthalene or Paradichlorobenzene is known in the art to be used to protect woollen and fur-feather lined articles from insect damage during their storage. But these above compounds are ineffective against clothes moths and thus unable to provide protection to the woollen items as established by Abbott & Billings of USA in 1935 and published their work in the Journal of Economic Entomology on page 493-495 as entitled "Further work showing that Paradichlorobenzene, Naphthalene and cedar oils are ineffective as repellents against clothes moth". The ineffectiveness of the naphthalene balls in protection of woollen articles from insect pests is also confirmed by the present inventors.

Further disadvantage of naphthalene balls being in solid forms have to be kept as such with a layer or two of the garment thereby providing limited protection through its vapours. Also, these balls cause discolouring of the woollen items when-placed directly on the woollen item for long period. These balls provide no protection to the woollen items, fur and feather lined garments and other keratinous items from insect pests when kept in open, as balls require airtight container. Thus, there is a need to develop new antibacterial drugs with novel mechanism of action.

Application No. 2313/CHENP/2007 discloses a pharmaceutical formulation for delivery in aerosol or spray form, comprising a liquefied propellant gas, a solid particulate pharmaceutically active agent and a dispersing agent, wherein the dispersing agent is fused to the surface of particles of the pharmaceutically active agent.

U.S. Pat. No. 5,178,872 discloses an insecticidal and/or acaricidal and/or nematicidal composition having a rapid efficacy and residual activity which comprises a mixture of a poorly water-soluble organophosphorus insecticide and/or acaricide and/or nematicide and/or a poorly water-soluble carbamate insecticide and/or acaricide which have been microencapsulated in water-insoluble polymer coatings with a dispersing agent used in forming a microcapsule part, with a poorly water-soluble pyrethroid insecticide and/or acaricide emulsified or suspended in water with the above-mentioned dispersing agent used in forming a flowable part.

US 2008/0090780 A1 discloses a storage stable, efficacious pesticide formulation is provided that is dilutable by the user and contains azadirachtin (AZA) and a pyrethrin or pyrethroid (PYR), and optionally an aprotic solvent and nonionic, substantially water-free emulsifier. A sufficient amount of the PYR is provided to complex with the AZA A on opposite sides of the molecular structure thereof, thereby preventing rearrangement of the AZA A molecule in the presence of moisture that would result in hydrolysis and decomposition of AZA A. The AZA-PYR combination is sufficiently chemically stable such that less than 10% of the AZA A is decomposed when the formulation is subjected to an accelerated aging test for 30 days at 40° C. in a sealed container. The molar ratio of PYR to AZA A is preferably within the range of 0.5/1-10.5/1, more preferably within the range of 1.5/1-7/1, and most preferably with the range of 3/1-6/1. A solvent, when provided, should be in the range of about 70% to about 90% by weight based on the weight of the formulation, and the emulsifier should be within the range of about 0% to about 20%.

WO 1997/00610 discloses an insect-attracting insecticidal aerosol spray composition containing an insect-attracting effective amount of 1 to 10% w/w of lauric acid, d-limonene, orange oil or mixtures thereof. The composition provides a long lasting barrier protection. It maintains the attractancy for a period of 13 weeks or more.

A method of treating carpet and other textile products comprising animal fibres or a mix of synthetic fibres and animal fibres is disclosed in WO/1997/023682. The method includes applying a formulation to carpet or other textile products. The formulation comprises compounds effective against the larvae of a range of Coleopteran species and a chemical which is effective against the larvae of a range of Lepidopteran species. The fluorosurfactant compound can offer only partial control of the larvae of a range of Lepidopteran species. The formulation can be added to the carpet, yarn, loose fibre or other textiles during raw-wool scouring, dyeing, tapescouring, chemsetting or continuous carpet treatment.

Microcapsule for smart textile materials, containing an active product and with reactive groups, with the objective of chemically binding the microcapsules to the fibres is disclosed in WO 2006/117702. The microcapsules contain active products such as PCM (phase change materials), or can be of controlled release of products such as fragrances, essential oils, antibacterial and others with the objective to add specific functional properties to the textile materials. They can be applied by padding and spraying followed by thermo fixation. In case of products such as knitwear the application process can also be by exhaustion process, given that the microcapsules acquire affinity towards the fibres and react with the fibres during the process. The chemical bond of the controlled release microcapsules with the fibres confers them a higher resistance to washing than the existing microcapsules glued to the fabric by printing or padding.

WO 2006/107905 discloses pesticide concentrates are provided containing an emulsifier that is an EPA list 4 inert and is a polyglycerol fatty acid ester, a sorbitan fatty acid ester or a combination thereof, a pesticide and a solvent that is either a EPA list 3 inert of acetyl ester, EPA list 4 inert of a methyl fatty ester, an acetyltributyl citrate, white mineral oil or a combination thereof. The pesticide can be a water-insoluble synthetic pyrethroid, natural pyrethrum, channel blocking insecticide, acetylcholinesterase inhibitor, oxadiazine, organophosphate, neonicotinoid insecticide, thiamethoxam, imidacloprid, acetamiprid, thiacloprid, clothianidin, nitenpyran, insect growth regulator, juvenile hormone mimic, fermentation insecticide, plant oil insecticide, acaracide, miticide, fungicide, herbicide and combinations thereof. The pesticide concentrate is diluted with a hydrocarbon solvent, a white mineral oil or a combination thereof and mixed with water. A corrosion inhibitor is added to form a stable water-in-oil emulsion in conjunction with a propellant to make a ready-to-use aerosol for home, garden and public health pest control.

Thus, there is a need to develop a new insecticidal composition for protection of woollen articles made of pure (100%) wool fibres or blended with natural or synthetic fibres like polyester, viscose rayon, cotton, etc. or both in different proportion such as apparel, carpet, durries, felt etc. and fur-feather lined garments that are highly susceptible to insect damage, and are frequently damaged or destroyed by various insect species of wool pests in commercial, industrial and domestic stores and also during their use and transport.

OBJECTS OF THE PRESENT INVENTION

The primary object of the present invention is to provide aerosol spray solution composition which provides highly effective protection to woollen items and other keratinous articles, from various insect species of wool pests i.e. both against carpet beetle types as well as against clothes moth type of insect pests throughout period of their storage, use and transport.

Another primary object of the present invention is to provide an aerosol spray solution composition which can be applied easily on the woollen items, fur and feathers lined garments and other keratinous goods at industry commercial and domestic stores for at least two years.

The objective of present invention is to provide low volatility and dry-cleaning fastness aerosol spray-solution.

Yet another primary object of the present invention to provide an aerosol spray solution composition which causes no stain or any colouring/decolouring when sprayed on woollen items and other keratinous items.

Another object of the present invention is to provide a aerosol spray solution composition which is effective against pests at different stages of their life cycle such as egg, larva and adult.

Further object of wool care aerosol spray solution composition is to provide spray solution which is such that the fabrics, garments sprayed with this solution when put on by humans do not cause any allergy to the wearer of the garment or to the person who sprays the solution.

Still further object of wool care spray solution composition is to provide insecticide spray solution which restricts the evaporation of the solvent isopropyl alcohol or mineral turpentine oil (MTO) or white spirit which is otherwise highly volatile-thereby ensuring that the concentration of insecticide in the solution remains constant during storage.

Yet further object of wool care aerosol spray composition is to provide insecticide spray solution which even sprayed on the woollen items forms a thin film over the surface of the woolen items, which retains insecticide for longer duration.

Still further object of wool care aerosol spray composition is to provide insecticide spray solution which when sprayed does not in any way alter the overall texture or appearance of the woollen garments fur and feather lined goods and other keratinous items.

Further another object of wool care aerosol spray solution is to provide spray which is behaviorally acceptable with pleasant fragrance to the user.

Yet further object of wool care aerosol spray solution is chemical loading of only required dose at industry level on finished fabric or garments and other keratinous items so that wastage of the insecticide solution could be avoided.

Another object of the wool care aerosol spray solution is for application of just sufficient chemical on the finished woollen fabrics at industry level to avoid application of insecticide for insect proofing at various fabric manufacturing stages such as dye bath and last scouring, etc so that water discharge from industry should be free from insecticide pollutant. This can be environmentally beneficial.

Yet another object of wool care aerosol spray solution is to be used easily in the ready to use aerosol spray having a hydrocarbon propellant, or by manually operated sprayer.

Further object of the wool care aerosol spray solution is that whereas the present spray solution can be uniformly sprayed on to the surface of the garment and provides uniform protection to the garment when kept in layers.

SUMMARY OF THE INVENTION

The present invention provides a wool care composition comprising of a pyrethroid insecticide (0.01-0.5% v/v); at least a copolymer (10-25% v/v); a solvent (70-85% v/v); and optionally a fragrance or a mixture of fragrances (1-5% v/v). It also provides a wool care composition comprising pyrethroid insecticide (0.01-0.5% v/v), a copolymer mixture comprising acrylic acid and butyl acrylate (10-25% v/v); and mineral turpentine oil as solvent (70-85% v/v), wherein said acrylic acid and butyl acrylate binds with said mineral turpentine oil and pyrethroid insecticide to enable prolonged storage of wool for at least 60 months. The pyrethroid insecticide used is preferably deltamethrin or permethrin.

The present invention further provides a wool care composition further comprising 20-30% v/v of at least a propellant.

These and other features, aspects, and advantages of the present subject matter will become better understood with reference to the following description and appended claims. This Summary is provided to introduce a selection of concepts in a simplified form. This Summary is not intended to identify key features or essential features of the claimed subject matter, nor is it intended to be used to limit the scope of the claimed subject matter.

DETAILED DESCRIPTION

The present relates to a wool care composition comprising a pyrethroid insecticide (0.01-0.5% v/v); at least a copolymer (10-25% v/v); a solvent (70-85% v/v); and optionally a fragrance or a mixture of fragrances (1-5% v/v). The copolymer in the composition of the present invention, binds with the solvent and pyrethroid insecticide to enable prolonged storage of wool for at least 60 months.

In an embodiment of the present invention, the composition comprises a pyrethroid insecticide (0.01-0.5% v/v); a copolymer (10-25% v/v); and a solvent (70-85% v/v); wherein said copolymer binds with the solvent and pyrethroid insecticide to enable prolonged storage of wool for at least 60 months.

In another embodiment of the present invention, the pyrethroid insecticide is a class of synthetic pyrethroid selected from deltamethrin and permethrin. The copolymer used in the composition is acrylic acid and butyl acrylate. Further in another embodiment, the copolymer of acrylic acid and butyl acrylate is in the ratio of 1:3 v/v.

In another embodiment, the solvent used in the composition of the present invention is selected from a group consisting of isopropyl alcohol, mineral turpentine oil (MTO) and white spirit, preferably, mineral turpentine oil.

In yet another embodiment, the fragrance used in the composition is selected from Alpha amyl cinnamic aldehyde, Dimetol, Terpeneol, Citronellol, Cedarwood oil, Lemon oil, Benzyl salicylatde, Tonalid, Ethyl vanillin, Cyclamen aldehyde, sandal wood oil and creosote.

The composition of the present invention can be formulated as a solution, with or without propellant.

In one embodiment, the wool care composition of the present invention further comprises of 20-30% v/v of at least a propellant, which forms another embodiment of the invention. This propellant is selected from a group consisting of C3-C5 alkanes or a mixture thereof. In a preferred embodiment, the propellant comprises of propane (6-12% w/v), n-butane (50-55% w/v) and isobutane (25-39% w/v).

In another preferred embodiment of the present invention, a wool care composition comprises pyrethroid insecticide (0.01-0.5% v/v), a copolymer mixture comprising acrylic acid and butyl acrylate (10-25% v/v); and mineral turpentine oil as solvent (70-85% v/v), wherein said acrylic acid and butyl acrylate binds with said mineral turpentine oil and pyrethroid insecticide to enable prolonged storage of wool for at least 60 months. The pyrethroid insecticide is preferably deltamethrin or permethrin.

The present invention provides a wool care aerosol spray solution composition, an effective amount of which can be sprayed, to kill various species of wool pests. Highly effective-insecticide, synthetic pyrethroid (s) is used as an agent for control of the wool insects and pests in this solute composition. The wool care aerosol spray solution incorporates emulsifier/copolymers and odours/fragrances which are then dissolved with 70-85% v/v of isopropyl alcohol or Mineral turpentine oil (MTO) or white spirit, to which is added a synthetic pyrethroid insecticide such as permethrin, cypermethrin, fenvalerate, deltamethrin, lambda-cyhalothrin or any mixture these insecticides, preferably deltamethrin or permethrin in the range of 0.01-0.5% v/v. The solution of the above chemical solution composition can be uniformly sprayed on to woollen items for providing protection from various species of insects and pests. Co polymer used binds the mineral turpentine oil/white spirit due to the higher viscosity and has the synergic effect of maintaining the concentration of the insecticide in the solution and remains ready for use even after prolonged storage. The copolymer forms a thin film that binds the insecticide and solvent MTO and spread evenly over the garment surface retaining the insecticide for longer period. Thus the woollen garments remained protected for about 60 months of unattended storage after the spray of this insecticide. The copolymer prevents deep penetration because of its high viscosity into the woollen fabric making available the insecticide at the very surface of the fabric, allowing no ingress to wool insects and pests. Odours/fragrances are advantageously selected in such a way that they enhance the repellent activity of the composition against the insect pests and at the same time it make more acceptable to the user as having pleasant smell.

The propellant is advantageously selected in such a way that it provides the desired pressure for uniform delivery of the wool care aerosol spray solution while spraying on the woollen items. Preferred propellants according to the invention are alkanes containing 3 to 5 carbon atoms, such as propane, n-butane, iso-butane, n-pentane and iso-pentane, n-butane and propane are particularly preferred for ready to use aerosol can.

The present invention relates to an improved aerosol spray composition for high effective protection (insect proofing) of pure or blended woollen item, fur and feather lined garments, and other keratinous items from various species of insect pests, more specifically but without implying any limitation thereto.

One aspect of the present invention relates to providing an aerosol spray solution composition which can be applied easily on the woollen items, fur and feathers lined garments and other keratinous goods at industry commercial and domestic stores for at least two years and thereto, to protect such items, during their storage, use and transport.

While various embodiments and/or individual features of the present invention have been illustrated and described, it would be obvious to those skilled in the art that various other changes and modifications can be made without departing from the spirit and scope of the invention. As will be also be apparent to the skilled practitioner, all combinations of the embodiments and features taught in the foregoing disclosure are possible and can result in preferred executions of the present disclosure. (Disclaimer)

EXAMPLES

1) Working Example

The following example is put forth so as to provide those of ordinary skill in the art with a complete disclosure and the description of how to make and use the present invention, and are not intended to limit the scope of what the inventors regard as their invention nor are they intended to represent that the experiments below are all and only experiments performed.

First, a co-polymer solution is prepared by mixing 10 ml of acrylic acid in 30 ml of butyl acrylate. Then 15 ml of this co-polymer solution was mixed 65-70 ml of Isopropanol or mineral turpentine oil or white spirit. To this 80-85 ml solution, 3-5 ml of odours fragrances and 5-10 ml of synthetic pyrethroid insecticide were added which was then thoroughly mixed with stirrer. This insecticide spray solution was poured into a hand sprayer for spraying on woollen fabrics/garments or in ready to use aerosol container.

The preparations according to the invention are produced and made up in the conventional manner known to the person skilled in the art. Initially, therefore, insecticide, emulsifiers (copolymers) and odours/Fragrances are thoroughly mixed with solvent. This mixture is then poured into aerosol cans in liquid form. After the valve has been applied, the propellant is finally added as the last component in the case of ready to use aerosol spray.

Laboratory evaluation of this insecticidal solution was carried out as per the international standardization method (ISO 3998) by releasing 15 larvae of each species on treated wool fabric pieces of 4 cm diameter size for 14 days in a Petri dish with a perforated lid. It was observed that tile larvae of tile said insect pests did not cause any damage to tile fabric during this period.

In, another laboratory evaluation test, 10 mated female adults of each insect species were released in a 0.25 liter glass jar on a 5 cm diameter treated wool fabric pieces which substantially covered the bottom of the jar and mouth was covered with a muslin cloth held by a rubber band. Cent percent adults of the insect pests died within 24 hours of exposure and no fabric damage was observed after six weeks on treated fabrics as laid eggs of pest were killed before larval emergence. The storage stability studies showed that treated fabric/garments with tills insecticidal spray protect them from insect/pest damage up to 60 months in stores.

It is to be understood that the spray formulation of the present invention is susceptible to modifications, adaptations and changes by those skilled in the field of the present invention. Such modifications, adaptations and changes are intended to be covered within the scope of present invention which is set forth by the following claims.

2) Example

Bioefficacy Tests of Wool Care Solution

Laboratory evaluation of this wool care spray solution was carried out as per the international standardization method (ISO 3998) by releasing 15 larvae of each species on treated wool fabric pieces of 4 cm diameter size for 14 days in a Petri dish with perforated lid. It was observed that the larvae of the two common and serious insect pests did not cause any damage to the wool fabric after spraying with wool care solution up to 24 months of storage as shown below in the Table 1 & 2. A test fabric is considered satisfactorily insect proofed if all four test specimens have no holes or surface damage (cropping) visible to unaided eyes and the mean weight loss for test specimens and the weight loss for single specimens are less that 15 mg and 20 mg respectively.

TABLE 1

Effectiveness of wool care solution against two common wool pests *Tinea translucens* and *Anthrenus flavipes* after treatment.

| Treatment | *Tinea translucens* | | | | *Anthrenus flavipes* | | | |
|---|---|---|---|---|---|---|---|---|
| | Visible Damage | | Mean Wt | | Visible Damage | | Mean Wt | |
| | Cropping[a] | Holes[b] | loss mg[c] | Status | Cropping[a] | Holes[b] | loss mg[c] | Status |
| Wool care | 1 | A | 1.70 | Proofed Control | 1 | A | 2.72 | Proofed |
| Treated with solvent | 3-4 | D | 85.06 | Not Proofed | 3-4 | D | 83.74 | Not proofed |
| Untreated | 3-4 | D | 91.9 | Not proofed | 4 | D | 93.92 | Not proofed |

TABLE 2

Effectiveness of wool care solution against two common wool pests of *Tinea translucens* and *Anthrenus flavipes* after treatment had aged 24 months.

| Treatment | *Tinea translucens* | | | | *Anthrenus flavipes* | | | |
|---|---|---|---|---|---|---|---|---|
| | Visible Damage | | Mean Wt | | Visible Damage | | Mean Wt | |
| | Cropping[a] | Holes[b] | loss mg[c] | Status | Cropping[a] | Holes[b] | loss mg[c] | Status |
| Wool care | 1 | A | 1.85 | Proofed Control | 2 | A | 5.50 | Proofed |
| Treated with solvent | 4 | D | 74.35 | Not Proofed | 4 | D | 100.42 | Not proofed |
| Untreated | 4 | D | 111.44 | Not proofed | 4 | D | 101.65 | Not proofed |

[a]Cropping (surface damage): 1-Not detectable; 2-Very slight; 3-Moderate; and 4-Very heavy.
[b]Holes: A-Not detectable damage; B-Yarns partially severed; C-Few small holes and D-Several large holes.
[c]Mean weight loss in four test replicates by the feeding of the test insect larvae.

Another laboratory evaluation test was also carried out to determine the pests' repelling or killing efficacy of wool care spray solution by releasing 10 mated female adults of each insect species in a 0.25 liter glass jar on a 5 cm diameter wool fabric pieces sprayed with wool care solution. The bottom of the jar was substantially covered with the treated fabric piece and mouth was covered with a muslin cloth held by a rubber band to force the adult pests to come in contact with the treated fabric. It was observed that the adult pest remain away from the treated fabric. All adults of the insect pests died within 24 hours of exposure and no fabric damage was observed after six weeks on treated fabrics as laid eggs of pest were also killed before larval emergence. The storage stability studies showed that treated fabric/garments with this wool care solution spray protect them from insect/pest damage up to 60 moths in stores.

METHOD OF USE

"Wool care" aerosol spray solution can be sprayed on woollen uniforms, blankets, jerseys, rugs, carpets, upholstery items and other woollen items before their storage or during their packing for transportation either with a ready to use aerosol container having a propellant or with manually operated sprayer. For treatment with wool care aerosol spray, the woollen items can be spread on a cloth line or on the ground, and then gently spray the solution in fine aerosol drops from a distance of 15-30 cms on the exteriors of woollen items. Spray of wool care solution should be light without drenching them or run off.

ADVANTAGES OF THE PRESENT INVENTION

The previously described versions of the subject matter and its equivalent thereof have many advantages, including those which are described below
  i. The present invention discloses binding of the copolymer to mineral turpentine oil/white spirit due to its high viscosity, resulting in a synergistic effect thereby maintaining the concentration of the insecticide in the solution permitting it to be used as a ready-to-use even after prolonged storage.
  ii. The present invention further relates to formation of a thin film of copolymer that binds the insecticide and solvent mineral turpentine oil (MTO), thereby spreading evenly over the garment surface retaining the insecticide for longer period, protecting for about 60 months of unattended storage after the spray of the insecticide. (Refer to example 2—Bioefficacy Tests of Wool Care Solution)
  iii. The present invention further discloses that the high viscosity of copolymer prevents deep penetration of the spray solution into the woollen fabric, thereby enabling availability of the insecticide at the very surface of the fabric, allowing no ingress to wool insects and pests.
  iv. The present invention also discloses that the selection of propellant is advantageous in such a way that it provides the desired pressure for uniform delivery of the wool care aerosol spray solution while spraying on the woollen items.

Although the subject matter has been described in considerable detail with reference to certain preferred embodiments thereof, other embodiments are possible. As such, the spirit and scope of the appended claims should not be limited to the description of the preferred embodiment contained therein.

We claim:

1. A wool care composition comprising:
   a. 0.01-0.5% v/v of a pyrethroid insecticide;
   b. 10-25% v/v of at least a copolymer of acrylic acid and butyl acrylate;
   c. 70-85% v/v of a solvent selected from the group consisting of isopropyl alcohol, mineral turpentine oil (MTO) and white spirit; and
   d. optionally 1-5% v/v of a fragrance or a mixture of fragrances.

2. The composition as claimed in claim 1, wherein the composition provides at least 60 months storage time for treated wool.

3. The composition as claimed in claim 1, wherein the pyrethroid insecticide is deltamethrin or permethrin.

4. The composition as claimed in claim 1, wherein the acrylic acid and butyl acrylate in the copolymer are in the ratio of 1:3 v/v.

5. The composition as claimed in claim 1, wherein the solvent is mineral turpentine oil.

6. The composition as claimed in claim 1, wherein the fragrance is selected from the group consisting of Alpha amyl cinnamic aldehyde, Dimetol, Terpineol, Citronellol, Cedarwood oil, Lemon oil, Benzyl salicylate, Tonalid, Ethyl vanillin, Cyclamen aldehyde, sandal wood oil and creosote.

7. The composition as claimed in claim 2, wherein the acrylic acid and butyl acrylate in the copolymer are in the ratio of 1:3 v/v.

8. The composition as claimed in claim 1 further comprising a propellant.

9. The composition as claimed in claim 8, wherein the propellant is a C3-C5 alkane or mixtures thereof.

10. The composition as claimed in claim 8, wherein the propellant comprises at least one component selected from the group consisting of propane (6-12% w/v), n-butane (50-55% w/v), isobutane (25-39% w/v) and mixtures thereof.

11. The composition as claimed in claim 9, wherein the propellant comprises at least one component selected from the group consisting of propane (6-12% w/v), n-butane (50-55% w/v), isobutane (25-39% w/v) and mixtures thereof.

12. The composition as claimed in claim 2, further comprising a propellant.

13. The composition as claimed in claim 4, further comprising a propellant.

14. The composition as claimed in claim 5, further comprising a propellant.

15. The composition as claimed in claim 6, further comprising a propellant.

16. The composition as claimed in claim 1, wherein the composition is formulated as a solution.

17. The composition as claimed in claim 8, wherein the composition is formulated as a solution.

18. A process for protecting wool from pests said process comprising applying to wool a composition of 0.01-0.5% v/v of a pyrethroid insecticide; 10-25% v/v of at least a copolymer of acrylic acid and butyl acrylate; 70-85% v/v of a solvent; and optionally 1-5% v/v of a fragrance or a mixture of fragrances.

* * * * *